(12) United States Patent
Larsen et al.

(10) Patent No.: US 6,592,843 B2
(45) Date of Patent: Jul. 15, 2003

(54) RADIOACTIVE THERAPEUTIC LIPOSOMES

(75) Inventors: Roy H. Larsen, Bekkestua (NO); Gjermund Henriksen, Mjondalen (NO)

(73) Assignee: Anticancer Therapeutic Inventions AS, Oslo (NO)

( * ) Notice: Subject to any disclaimer, the term of this patent is extended or adjusted under 35 U.S.C. 154(b) by 0 days.

(21) Appl. No.: 09/790,260

(22) Filed: Feb. 21, 2001

(65) Prior Publication Data

US 2001/0048914 A1 Dec. 6, 2001

(30) Foreign Application Priority Data

Feb. 21, 2000 (NO) ................................. 000855
Feb. 21, 2001 (WO) ................................ PCT/NO01/00065

(51) Int. Cl.$^7$ ........................ A61K 51/00; A61K 9/127
(52) U.S. Cl. ...................................... 424/1.21; 424/450
(58) Field of Search ........................ 424/1.21, 1.29, 424/9.321, 9.51, 450

(56) References Cited

U.S. PATENT DOCUMENTS 4,310,506 A * 1/1982 Baldeschwieler et al. ... 424/1.21
5,608,060 A * 3/1997 Axworthy et al. ........... 540/474

FOREIGN PATENT DOCUMENTS

EP 0 386 146 B1 9/1990

OTHER PUBLICATIONS

Deal et al., "Improved in vivo Stability of Actinium–225 Macrocyclic Complexes," *J. Med. Chem.* 42:2988–2992 (1999).
Bartlett, "Phosphours Assay in Column Chromatography," *J. Biol. Chem.*, 234:466–468 (1958).
Cabell, "The Purification, Determination, And Neutron Capture Cross Section Of Actinium–227," *Can. J. Chem.*, 37:1094–1103 (1959).
Dietz et al., "Improved Chemistry for the Production of Yttrium–90 for Medical Applications," *Appl. Radiat. Isot.*, 43:1093–1101 (1992).
Forssen, "The Design and Development of DaunoXome® for Solid Tumor Targeting In Vivo," *Adv. Drug Delivery Rev.*, 24:133–150 (1997).
Gabizon et al., "Targeting Folate Receptor with Folate Linked to Extremities of Poly(ethylene glycol)–Grafted Liposomes: In Vitro Studies," *Bioconjugate Chem.*, 10:289–298 (1999).
Gabizon, "Liposome Circulation Time and Tumor Targeting: Implications for Cancer Chemotherapy," *Adv. Drug Delivery Rev.*, 16:285–294 (1995).
Gaze, "The Current Status of Targeted Radiotherapy in Clinical Practice," *Phys. Med. Biol.*, 41:1895–1903 (1996).
Goins et al., "Repeat Injection Studies of Technetium–99M–Labeled PEG–Liposomes in the Same Animal," *J. Liposome Res.*, 8:265–281 (1998).
Hall, "Radiobiology for the Radiologist," Fourth Edn. J.B. Lippincott Company, 153–164 (1994).
Hassfjell et al., "A Generator for Production of $^{212}$Pb and $^{212}$Bi," *Appl. Radiat. Isot.*, 45:1021–1025 (1994).
Henriksen et al., "Isolation of Cyclotron Produced $^{205}$Bi, $^{206}$Bi and $^{203}$Pb Using a Lead–Selecting Extraction Chromatographic Resin," *Appl. Radiat. Isot.*, 49:357–359 (1998).
Hwang et al., "Fate of Lipid Vesicles In Vivo: A Gamma–Ray Perturbed Angular Correlation Study," *Proc. Natl. Acad. Sci. USA*, 74:4991–4995 (1977).
Kirpotin et al., "Sterically Stabilized Anti–HER2 Immunoliposomes: Design and Targeting to Human Breast Cancer Cells In Vitro," *Biochemistry*, 36:66–75 (1997).
Kostarelos et al., "Liposome–Mediated Delivery of Radionuclides to Tumor Models for Cancer Radiotherapy: A Quantitative Analysis," *J. Liposome Res.*, 9:407–424 (1999).
Larsen et al., "The Cytotoxicity and Microdosimetry of Astatine–211–Labeled Chimeric Monoclonal Antibodies in Human Glioma and Melanoma Cells In Vitro," *Radiat. Res.*, 149:155–162 (1998).
Lee et al., "Delivery of Liposomes into Cultured KB Cells via Folate Receptor–Mediated Endocytosis," *J. Biol. Chem.*, 269:3198–3204 (1994).
MacDonald et al., "Small–Volume Extrusion Apparatus for Preparation of Large, Unilamellar Vesicles," *Bioch. Biophys. Acta*, 1061:297–303 (1991).
Maruyama et al., "Targeting Efficiency of PEG–Immunoliposome–Conjugated Antibodies at PEG Terminals," *Adv. Drug Delivery Rev.*, 24:235–242 (1997).
Mauk et al.,"Preparation of Lipid Vesicles Containing High Levels of Entrapped Radioactive Cations," *Anal. Biochem.*, 94:302–307 (1979).
McClure et al., Alpha–Emitters for Medical Therapy: Second Bi–annual Workshop, Toronto, Canada, Jun. 4–5. Report from Department of Energy, Germantown, MD, USA. DOE/NE–0116:1–25 (1998).
Mirzadeh et al., "The Chemical Fate of $^{212}$Bi–DOTA Formed by $\beta^-$–Decay of $^{212}$Pb(DOTA)$^{2-}$," *Radiochimica Acta*, 60:1–10 (1993).

(List continued on next page.)

Primary Examiner—Michael G. Hartley
(74) *Attorney, Agent, or Firm*—Clark & Elbing LLP (57) ABSTRACT

The present invention relates to a conjugator system comprising liposomes with ionophores, and with chelator solution and alpha-particle emitting radionuclide(s) located inside of the liposome. Furthermore, a the method for the preparation of this type of radioactive liposomes is described, as well as use of the system and a kit for preparing the system.

35 Claims, 2 Drawing Sheets

OTHER PUBLICATIONS

Ogihara–Umeda et al., "Optimal Radiolabeled Liposomes for Tumor Imaging," *J. Nucl. Med.*, 37:326–332 (1996).

Olson et al., "Preparation of Liposomes of Defined Size Distribution by Extrusion Through Polycarbonate Membranes," *Bioch. Biophys. Acta*, 557:9–23 (1979).

Pikul et al., "In Vitro Killing of Melanoma by Liposome–Delivered Intracellular Irradiation," *Arch. Surg.* 122:1417–1420 (1987).

Ritter et al., "High–LET Radiations Induce a Large Proportion of Non–Rejoining DNA Breaks," *Nature*, 266:653–655 (1977).

Tilcock et al., "An Improved Method for the Preparation of Liposomal Gadolinium–DTPA," *Invest. Radiol.*, 26:242–247 (1991).

Turner et al., "In–111–Labeled Liposomes: Dosimetry and Tumor Depiction," *Radiology*, 166:761–765 (1988).

Utkhede et al., "Uptake of Yttrium–90 Into Lipid Vesicles," *Journal of Liposome Research*, 4:1049–1061 (1994).

\* cited by examiner

RADIOACTIVE THERAPEUTIC LIPOSOMES

CROSS REFERENCE TO RELATED APPLICATIONS

This application claims benefit of Norwegian Patent Application No. 2000 0855, filed Feb. 21, 2000.

The present invention relates to a conjugator system comprising liposomes with ionophores and with chelator located inside of the liposomes, wherein the liposomes are stably labeled with heavy radionuclides emitting a particles. The present invention further relates to a method to prepare the conjugator system and use of the system, as well as a kit for preparing the conjugator system.

Biomedical applications of radionuclides in anticancer therapy have so far focused on the use of cationic or anionic species, e.g., [$^{131}$I]iodide against thyroid cancer and $^{89}$Sr for palliation of pain from skeletal cancer metastases, and the use of mostly beta-emitting radionuclides attached to monoclonal antibodies (DeVita et al., 1996).

The use of targeted radionuclide therapy against cancer rest upon the ability to find ways to attach radionuclides to tumor specific carrier compounds (Gaze, 1996). Today, some of the radionuclides with useful radiation characteristics cannot be used in tumor targeting because of the problem of providing a chemically stable link between the radionuclide and the carrier compound. Now carrier systems may, however, broaden both the use of radioisotopes, as well as the arsenal of radionuclides considered useful for therapy (Gaze, 1996).

Liposomes, with or without receptor affinic groups attached to the surface, have been evaluated for drug delivery, and is currently used clinically for the delivery of chemotherapeutics in some cancer forms. Recently, developments in liposome research have led to new versions with a pharmacokinetics which could make these compounds useful as carriers for radionuclide for internal radiotherapy against cancer (Gabizon, 1995). These recent developments in the formulation and manufacturing of liposomes have resulted in small vesicles of less than 100 nm with prolonged circulation time, as the size of the liposomes can be better confined to small diameters by using extrusion through membranes. Furthermore, the introduction of poly ethylene glycol (PEG) grafted liposomes has reduced the interference from plasma proteins, and thus reduced the recognition and clearance affected by the macrophages of the reticuloendothelial system (Maruyama, et al., 1997). Increased levels of tumor uptake due to sustained blood concentration have thereby been achieved. Even further tumor uptake has boon achieved by conjugating molecules with receptor affinity, e.g., monoclonal antibodies or folate, to the surface of the liposomes. In addition, several studies have indicated the advantage of applying PEG as a linker between the lipsome and the targeting ligand, since this also can improve the receptor accessibility (e.g. Maruyama et al, 1997; Gabison et al, 1999; Lee et al, 1994).

Liposomes have previously been studied as carriers for radioisotopes (Goins et al, 1998; Turner et al, 1988). Pikul, et al (1987) reported a study based on $^{212}$Pb-dextran incorporated passively (i.e., the $^{212}$Pb-dextran was added during the generation of the liposome, and a fraction of the $^{212}$Pb-dextran was incorporated together with the aqueous phase representing the interior of the liposome). The authors did not suggest that these liposomes were suitable for cancer therapy, but was using it primarily for studying intracellular cell killing in vitro with radioisotope. No data of the fate of $^{212}$Bi generated from the $^{212}$Pb decay was presented, and the size of the liposomes were in the order of 350–500 nm which is very large compared to the size (approx.100 nm) currently considered optimal for in vivo tumor therapy (Forssen, 1997). Also, the liposomes did not contain PEG in the membrane.

Ogihar-Umeda et al. (1996) used liposomes as carrier for the gamma emitting radionuclides $^{67}$Ga, $^{111}$In and $^{99m}$Tc, and suggested the use of radiolabeled liposomes for imaging.

In a theoretical study, Kostarelos et al. (1999) suggested the use of liposomes labeled with the potentially therapeutically radionucides $^{131}$I, $^{67}$Cu, $^{138}$Re and $^{211}$At, but chemical procedures for the preparation of the radiolabeled liposomes were not suggested.

EP386 146 B1 describes a composition and method of use for liposome encapsulated compounds for neutron capture tumor therapy. However, these liposomes were loaded with stabel elements (e.g. boron), that become radioactive only after activation, and the liposomes contain neither ionophores nor chelator.

Utkhede et al., (1994) describes liposomes loaded with $^{90}$Y and the chelator DTPA, which is a different chelator compared to the chelators described in the present invention. Furthermore, retention of mother/daughternuclide(s) is not described and in addition, $^{90}$Y is not a heavy element as the elements described in the present application.

Achieving sufficiently stable radiolabeling of carriers with heavy alpha-emitting radionuclides usually requires specific chemical procedures tailored to suit the chemistry of each element, and such methods are not known. Procedures used to radiolabel e.g. Ga, In, Te, Cu or Re cannot be expected to be compatible with heavy radionuclide (atomic weight over 150) cationic alpha emitters like e.g. $^{212/213}$Bi, $^{212}$Pb, $^{223/224}$Ra, $^{227Th}$ or $^{225}$Ac.

It is therefore an object of the present invention to provide a radionuclide-liposome conjugator system, with or without receptor affinic groups, that (1) encapsulates chelator and heavy radionuclide(s) that emit alpha particle radiation, (2) can retain daughter nuclide(s) when the mother nuclide(s) is incorporated in the liposome and (3) can be prepared by an active incorporation procedure useful for a panel of radionuclides, as well as use of the system and a kit for preparing the system These objects have been obtained by the present invention, characterized by the enclosed claims.

The present invention relates to a conjugator system comprising liposomes with ionophores, i.e., a metal extracting agent for liposomes, and with chelator and heavy radionuclide(s) (atomic weight over 150) located inside the liposome. The liposomes are prepared using active incorporation of the radionuclide, i.e., via ionophores, and prepared according to procedures yielding liposomes of size of typically 100 nm. The resulting product shows good chemical stability over several days, and may also retain daughter nuclide(s) inside the liposome, e.g. from the transformation of $^{212}$Pb to $^{212}$Bi. The liposomes can be prepared with or without modifying groups like polyalkylene oxides, e.g., PEG, attached to the membrane. Herein we also describe a method to link such radiolabeled liposomes to tumor seeking proteins, such as e.g. folate conjugated monoclonal antibodies.

The present invention will now be described in more detail, with reference to figures and examples.

Figure 1:
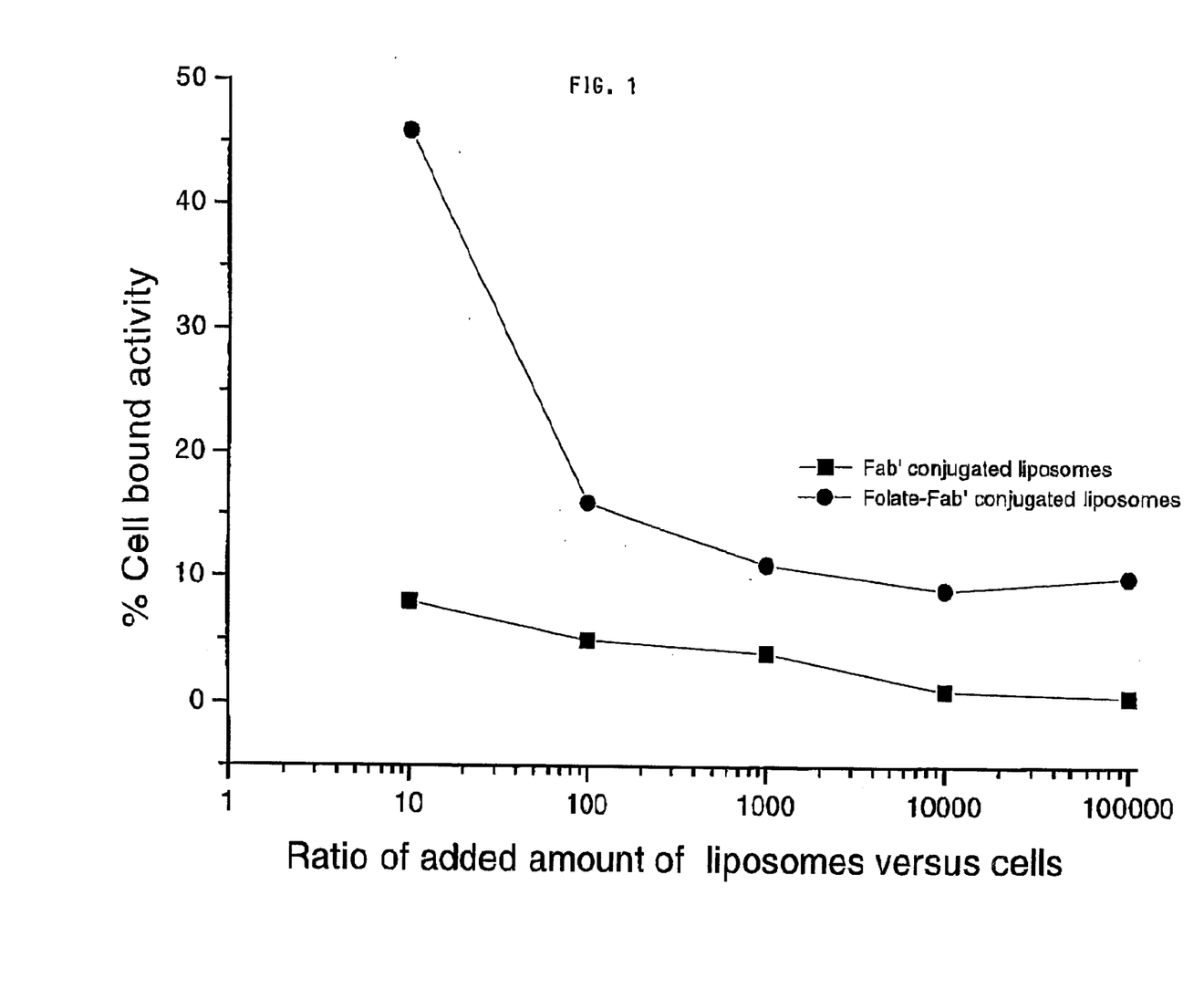
FIG. 1 Binding of PEGylated liposomes, containing either Fab' or folate-labeled Fab' antibody conjugated to the liposome membrane, to OVCAR 3 cells.
Figure 2:
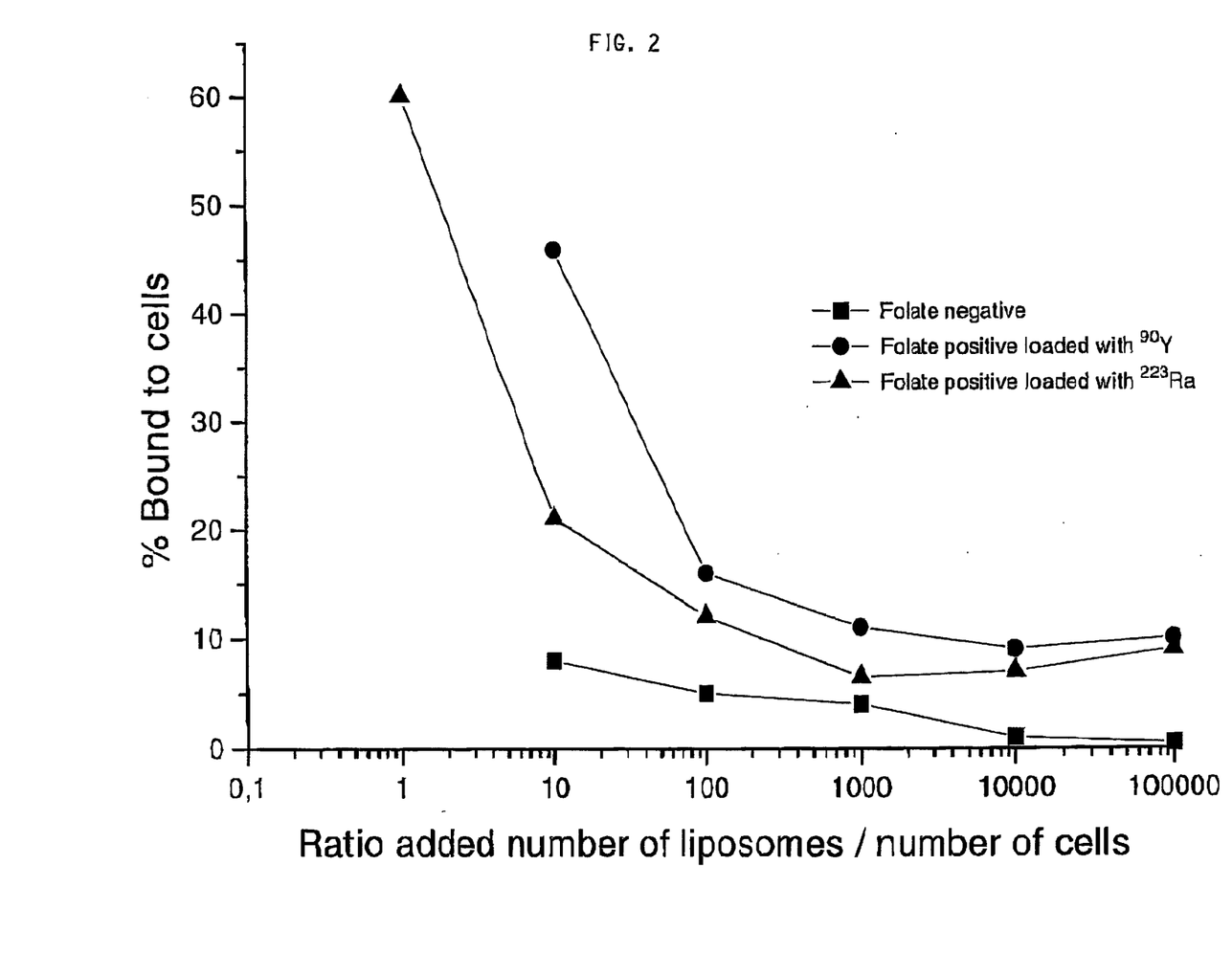
FIG. 2 Binding of folated versus non-folated PEG liposomes to OVCAR 3 cells.

In order to develop radiolabeled liposomes that are suitable for cancer therapy, the present inventors have studied the preparation and use of liposomes loaded with heavy radionuclides (i.e., atomic weight over 150) emitting alpha particles, based on the radionuclides $^{212}$Bi, $^{213}$Bi, $^{223}$Ra, $^{224}$Ra, $^{225}$Ac, $^{212}$Pb and $^{227}$Th. Using liposomes (vesicles) with ionophores, radiolabeled liposomes with preferably a chelator (i.e., the liposomes are encapsulating radionuclide and chelator) were prepared by use of active incorporation of the radionuclide, and prepared according to procedures yielding liposomes of a typical size of 100 nm.

Unilamellar vesicles were prepared by thin lipid film hydration and extrusion (Olson et al. 1979, Mac Donald et al. 1991) in the following manner: DSPC (distearoyl phosphatidyl choline) and cholesterol in a 2:1 molar ratio, typically 10 and 5 $\mu$mol, respectively, were dissolved in chloroform in a round bottom flask. The solvent was removed by rotary evaporation using reduced pressure. The dry lipid film was then hydrated in 0.5–1 ml of 150 mM citric acid, 30 mM DOTA (1,4,7,10 tetraazacyclododecane 1,4,7,10 N, N', N", N'''tetraacetic acid), pH 4. The resulting suspension was subjected to live cycles of freezing and thawing followed by repeated extrusion through polycarbonate filters of 100 nm pore size 5 times and of 50 nm pore size 5 times employing a manual extruding device (Avestin, Ottawa, Canada). The product had a lipid concentration of ~30 mM. Prior to radionuclide loading of the liposomes, the external solution was exchanged by elution on a PD-10 column for 250 mM sucrose, 20 mM HEPES (N-2-hydroxyethylpiperazine-N'-2 ethanesulphonic acid), pH 7.4.

Liposome constituents: a) Internal aqueous medium: pH 1–14, preferably 2–9, more preferably 4–5. Constituents: Water; agents capable of maintaining the desired pH in the internal aqueous medium for the desired time interval, i.e., until ionophore-mediated incorporation of radiometal(s) is initiated. Preferably, the constituents of the internal aqueous medium also leads to a comnplexing function of the radiometal(s). This can be brought to effect by i) e.g. electrostatic donor functions of the agents used for adjustment pH, e.g. the oxygen atom(s) in acetate, citrate and related compounds; ii) in addition, having a complexing agent in the internal aqueous medium, e.g. EDTA, DTPA, DOTA, DOTMP and related compounds.

b) Ionophore, e.g. agent capable of transporting, essentially irreversible, a radio metal across the lipid bilayer from the extraliposomal phase to the liposome interior. Examples: Ionophores showed to function in the desired manner: Calcium ionophore A 23187. Dicyclohexyl 18-C6, Bibenzo-18-C6, 2,3,-dimercapto-1-propanol, Pb-ionophore.

c) Constituents of the lipid bilayer: Constituents of the lipid bilayer preferably result in a mixture capable of forming vesicles, and for which the liquid-to-solid transition temperature is above the physiological temperature e.g., i) phospholipids. Examples; Long-chained, alkyl-phosphatidylcholines e.g. 1,2-dilauroyl-sn-glycero-3-phosphocholine (DLPC), 1,2-dinlyristoyl-sn-glycero-3-phosphocholine (DMPC), 1,2-dipalmitoyl-sn-glycero-3-phosphocholine (DPPC), 1,2-distearoyl-sn-glycero-3-phosphocholine (DSPC), 1,2-dioleoyl-sn-glycero-3-phosphocholine (DOPC), 1-palmitoyl-2-oleoyl-sn-glycero-3-phosphocholine (POPC); ii) sterols or compounds possessing similar properties in that they stiffens (decrease the fluidity of) the lipid bilayer. Examples: Compounds of the sterol class: Cholesterol and cholesterol 3-sulfate, and iii) (sterically) in vivo stabilizer(s) for increasing tumor-cell targeting properties of the construct and increasing the blood residence time, e.g. polyethers, polyethylene glycols. Inclusion of PEG and/or PEG derivatives in liposome formulations will offer advantages in terms of reduced clearance of injected liposomes from the circulatory system by the reticulo-endothelial system. Normally included in the preparation at 3–10 mol % relative to phospholipid. The amount of stabilizer necessary for obtaining the desired stabilizing effect is, however, dependent of the monomer (electrostatic and polar properties) and the number of repeating units i.e., the chain length. Examples (PEG and/or PEG derivatives) 1,2-dinlyristoyl-sn-glycero-3-phosphoethano lamine-N-[poly(ethylene glycol) 2000] (PEG2000 DJ\1PE), 1,2-dipalmitoyl-sn-glycero-3-phosphoethano lamine-N-[poly(ethylene glycol)2000] (PEG2000 DPPE), 1,2-distearoyl-sn-glycero-3-phosphoethano lamine-N-[poly(ethylene glycol)2000] (PEG2000 DSPE).

d) Constituents facilitating modification of constucts to possess tumor cell targeting properties: The choice of appropriate activated lipid will be determined by the nature of the hapten, as well as the requirements of the investigation. The efficiency of the reaction will be governed by the leaving group, hydrophilic spacer, material properties of the liposome, and the concentration of reactants. For in vivo investigations, in which the hapten is required to remain associated with the liposome, distinct advantages will be gained by choosing longer acyl chain lipid anchors which exchange more slowly between membranes. Further, the covalent bond between hapten and lipid anchor should be stable to both chemical and enzymatic cleavage. The activated lipids can function to form e.g. amine, amide, thioeter, or disulphide bonds between the lipid and modificator. If sterically stabilizers are included in the preparation, e.g. PEG and/or PEG derivatives, the group functioning for coupling is preferably present on the end of a compound equal or similar to the stabilizer and with an effective chain length equal to or longer of than that of the stabilizer. Examples: Vesicle constituents facilitating modification of constructs to possess tumor cell targeting properties from the PEG and/or PEG derivatives: N-[w-(2-pyridyldithiopropionylamino) poly(ethyleneglycol) 2000] 1,2-distearoyl-sn-glycero-3-phosphoethanolamine (PDP-PEG2000-DSPE), N-{w-[4-(p-maleimidophenyl)butanoyl]amino} poly(ethylene glycol) 2000] 1,2-distearoyl-sn-glycero-3-phosphoethanolamine (MpB-PEG2000-DSPE).

Separation of liposome associated radionuclide from non-associated radionuclide was achieved by the use of size-exclusion chromatography (Mauk and Gamble 1979, Tilcock et al. 1991). For the separations following liposome loading procedures, PD-10 size exclusion columns were employed. From applied volumes of 1 ml or less on the PD-10 columns, the liposomes eluted in the first 4.5 ml. Radionuclides not associated with liposomes eluted in the fraction corresponding to low molecular weight species. PD-10 columns were also used in the study of the stability (with respect to radionuclide retention) of the loaded liposomes in PBS.

The separation of liposome associated radionuclides from free radionuclides in the serum was performed by size exclusion chromatography on a Sepharose CL-4B column (Hwang and Mauk, 1977) Thereby solutions containing radioactive liposomes dispersed in a liquid carrier substancially free from unbound radionuclides could be prepared.

EDTA (ethylene diamine N, N' tetra acetic acid) was added prior to the chromatographic procedures to stabilize the free radionuclide in a state that could easily be separated from the liposome associated fraction.

The radionuclide loading yield for, and the latency of, the liposome associated radionuclides was established by gamma-spectroscopy for $^{228}$Ac, $^{223}$Ra, $^{212}$Pb, $^{212}$Bi, $^{205}$Bi and $^{207}$Bi. $^{228}$Ac and $^{205/207}$Bi were used as a tracer for the potentially therapeutically useful radionuclides $^{225}$Ac, $^{212}$Bi and $^{213}$Bi, respectively.

The present inventors made the significant and unexpected discovery that $^{212}$Bi did not translocate significantly after the decay of $^{212}$Pb incorporated in this type of liposomes. Current status for the use of $^{212}$Pb as a molecularly linked generator for $^{212}$Bi, indicates that a significant release ($\geq 30\%$) usually occurs from a chelator (McClure and Feinendegen, 1998; Mirzadeh et al., 1993). However, by trapping of the $^{212}$Pb in a high concentration of chelator, such as for example inside of the liposome, release of daughter product could be avoided providing a conjugator system that could be used to trap the daughter nuclide after nuclear transformation. This is the first time a conjugator system for $^{212}$Pb that could retain the $^{212}$Bi daughter nuclide almost quantitatively is reported. Thus, the present invention relates to liposomes with ionophores that comprises radionuclide and chelator located inside the liposome (conjugator system), and wherein this conjugator system can or cannot retain the daughter nuclide.

A chelator according to the present invention, can be selected from the group comprising 1,4,7,10 tetraazacyclododecane-1,4,7,10 N, N', N", N'"-tetraacetic acid (DOTA), 1,4,7,10 tetraazacyclotridecane-1,4,7,10 N, N', N", N'"-tetraacetic acid (TRITA), 1,4,7,10 tetraazacyclotetradecane-1,4,7,10 N, N', N", N'"-tetraacetic acid (TETA), 1,4,7,10 tetraazacyclododecane-1,4,7,10 N, N', N", N'"-tetra (methylene) phosphonic acid (DOTMP), 1,4,7,10 tetraazacyclotridecane-1,4,7,10 N, N', N", N'"-tetra (methylene) phosphonic acid, 1,4,7,10 tetraazacyclotetradecane-1,4,7,10 N, N', N", N'"-tetra(methylene) phosphonic acid, diethylene triamine N, N', N" pentaacetic acid and isomeric derivatives thereof, cryptate[2,2,2], cryptate[3,2,2], cryptate[2,2,1] and mono and di-benzo derivatives thereof, bridged calix[4]arenes containing electron rich (donor) groups (hydroxyl, carboxyl, ester, amid, amine), 1,10 diaza-4,7,13,16-tetraoxacyclooctadecane-1,10 N, N' bis-acetic acid, and 1,10 diaza-4,7,13,16-tetraoxacyclooctadecane-1,10 N, N' bis-malonate.

Another important and surprising discovery was that liposomes according to the present invention could incorporate and retain $^{223}$Ra efficiently. This is the first time that a conjugator system potentially useful for tumor targeting with radium-223 is described. In addition, we show that also bismuth and actinium can be incorporated and strongly retained in the presently described type of liposomes, indicating that conjugator systems based on $^{212}$Bi, $^{213}$Bi and $^{225}$Ac also can be prepared.

The conjugator system according to the present invention can be made with or without modifying surface groups, e.g., PEG, in the liposome membrane (PEG grafted/PEGylated liposomes). The advantage of applying PEG in the membrane is that it provides some PEG-reactive groups that allows conjugation of proteins such as e.g. antibodies, antibody fragments or constructs or folate, or other receptor affinic (receptor binding) proteins/molecules.

The present application further relates to a now type of liposomes with receptor binding proteins attached to the liposome membrane. Herein we describe radiolabeled PEG grafted liposomes conjugated to folate labeled antibodies. The use of folate and folate derivatives to target tumors expressing folate binding proteins (FBP), a glycosyl-phosphatidyl-inositol-linked cell membrane protein involved in cellular uptake of oxidized folates via endocytosis, has attracted attention among researchers (Kranz et al., 1996; Reddy et al., 1998; Shinoda et al., 1998; Trippet et al., 1999). As several types of human cancer cells have been shown to overexpress FBP, this receptor may be a possible target for delivery of therapeutic radioisotopes conjugated with folate. Thus, by using antibodies conjugated to folate, a targeted radionuclide therapy against cancer could be obtained. Furthermore, if the folate labeled antibody's antigen combining site is directed against a tumor associated antigen different from FBP, dual binding ability is achieved (i.e., affinity for both the antibody-antigen and FBP receptor is achieved). To our knowledge, this is the first time conjugation of folate-labeled antibodies is described.

The folate-labeled antibodies conjugated to the liposomes according to the present invention could further be labeled with a radionuclide or a mixture of different radionuclides in order to increase the radiotherapy.

The present invention shows that this new combination of folate labeled antibodies conjugated to liposomes can be used to target radionuclide(s) to cells expressing folate receptors. This is especially useful with alpha particle emitters, which are high linear energy transfer (high-LET) radiation emitters that are extremely cytotoxic to mammalian cells (Hall, 1994; Larsen et al., 1998; Ritter et al., 1977). However, an alpha radiation source can deliver radiation to a particularly small area compared to other types of radiation. Thus, if an alpha radiation source can be directed to a target tissue, tissue exposure to normal tissue can be reduced.

A conjugator system according to the present invention could also be used to target cells expressing e.g. estrogen receptor or testosterone receptor, by conjugating antibodies to estrogen or testosterone.

The labeled antibodies used according to the present invention are preferably of IgG or IgM class, and/or fragments and/or constructs (e.g. minibody) thereof. Furthermore, these antibodies and/or fragments and/or constructs could be murine, chimeric or fully humanized, polyclonal or monoclonal.

The present invention also relates to use of the conjugator system according to the present invention, to prepare a pharmaceutical solution suitable for injection or infusion into mammals, including humans, by intravenous and/or regional, and/or intratumoral route of administration. The pharmaceutical solution can be used in combination with a radioimmunoconjugate or several radioimmunoconjugates, and/or other forms of radiopharmaceutical therapy, chemotherapy, external beam therapy or surgery, to treat malignancies.

The present invention also relates to a method to use the conjugator system according to the present invention to treat malignancies such as e.g. brain-, lung-, cervix-, ovary- or breast cancer, or leukemia, lymphoma or malignant melanoma.

The present invention also relates to a kit for the preparation of the conjugator system according to the present invention, comprising a vial containing a liposome solution and a second vial containing radionuclide in a solution, that can be mixed to facilitate radiolabeling. In addition, this could be mixed with a third vial containing a proteins and/or molecules with receptor affinity to obtain a receptor affinic conjugator system.

Reagents and Equipment

Gamma-spectroscopy was performed using a germanium detector (Canberra, Meriden, Conn., USA) coupled to a multichannel analyzer (EG&G ORTEC, Oak Ridge, Tenn., USA). A Beckmann LS 6500 (Beckmann, Fullerton, Calif., USA) was used for liquid scintillation counting. DSPC and cholesterol purchased from Northern Lipids (Vancouver, Canada). Sephadex G-25 PD-10 columns (Amersham Pharmacia Biotech AB, Uppsala, Sweden) was used for the purification of radiolabeled liposomes The macrocyclic chelator DOTA was used as intra-liposomal chelator and was purchased from Macrocyclics (Richardson, Tex., USA). Ultrex grade $HNO_3$ (J. T. Baker, Phillipsburg, N.J., USA) and 6M HCl (Fisher Scientific, Pittsburgh, Pa., USA) and bis(2-ethyl hexyl) phosphoric acid (HDEHP) from Fluka (via Sigma-Aldrich AS, Norway) was used in the study.

All buffers used for the ionophore mediated cation loading of liposomes were adjusted to the desired pH using arginine (flee base). All water used was obtained from a Milli-Q water purification system (Millipore, Bedford, Mass., USA). Ion exchange resins were supplied by Bio-Rad (Hercules, Calif., USA).

The resins was preconditioned by washing with water, then 6 M HCl followed by acetone and finally with water. The resins were stored in water prior to column packing.

The DMSO used was stored with 4 Å sieves.

The $^{232}Th(NO_3)_4$ used in this work had been stored for more than 20 y. The sample was provided by Nuclear Chemistry Group, Department of Chemistry University of Oslo, Oslo, Norway.

$^3$H-folic acid was purchased from Amersham Pharmacia Biotech (Buckinghamshire, UK).

All other chemicals were purchased from Sigma-Aldrich, Norway.

Table 1 shows some physical properties of radionuclides used in experiments with liposomes.

TABLE 1

| Nuclide | $t_{1/2}$ | gamma-ray(s) | % probability |
|---|---|---|---|
| $^{228}$Ac | 6.13h | 911.2 (26.6) | 26.6 |
| $^{223}$Ra | 11.43d | 269.4 (13.7) | 13.7 |
|  |  | 271.2 (0.108) $(^{219}Rn)^2$ | 10.8 |
| $^{212}$Pb | 10.6h | 238.6 (43.6) | 43.6 |
| $^{208}$Tl | 3.05m | 583.1 (32.5) | 35.2 |
| $^{207}$Bi | 31.55y | 569.7 (97.7) | 97.7 |
| $^{205}$Bi | 15.31d | 703.4 (31.1) | 31.1 |

*Only the most abundant gamma-ray is listed for each radionuclide.
Data from Nuclear Data Sheets, Academic Press INC.

Best Mode

Liposomes prepared according to the described procedures were loaded with radium-223 or lead-212. Thereafter, antibodies were reacted with liposomes to achieve antibody molecules on the surface of the liposomes. Lipsome size of about 100 μm will be appropriate for systemic delivery, but typical sizes of 200–1000 μm can be used when intracavitary delivery, e.g., for the treatment of intracranial brain tumor, or for the treatment of intraperitoneal ovarian cancer, is to be achieved. (The larger liposome size could slow down clearance rate from the cavity where the preparation is injected, thereby maintaining a high concentration in the tumor region.)

EXAMPLES

Example 1

Loading of $^{212}$Pb/$^{212}$Bi in Liposomes

Methods: $^{212}$Pb/$^{212}$Bi was produced via emanation of $^{220}$Rn from a $^{228}$Th source as described by Hassfjell and Hoff (1994). No carrier added $^{212}$Pb/$^{212}$Bi was leached from the collection vessel using 0.1 M $HNO_3$, and the solution applied to a 2×20 mm column of AG 50W-X4 cation exchange resin. $^{212}$Pb/$^{212}$Bi was then eluted in 2 M HCl and the solution evaporated to dryness. The $^{212}$Pb/$^{212}$Bi was then dissolved in 200 μl 10 mM acetate solutions pH 5. $^{212}$Pb was quantified by measurement of its 238.6 keV gamma-ray (Table 1). $^{212}$Bi was quantified by measuring the 583.1 keV gamma-ray of its daughter $^{208}$Tl at radioactive equilibrium.

Results. Less than 0.2% of the added activity was found to be associated with the liposomes for incubation times up to 3 days.

Liposomes corresponding to a lipid concentration of 30–60 mM was vigorously mixed with a film of the ionophore A23187 (10–13 nM). Approximately 1 MBq of $^{212}$Pb/$^{212}$Bi was then added and the mixture was incubated at 75° C. for 30 min. followed by elution on a PD-10 column. The fraction containing more than 95% of the loaded vesicles was then eluted on a second PD-10 column. The latency of the liposome associated $^{212}$Pb/$^{212}$Bi was investigated by incubating the vesicles at 37° C. in human serum or PBS. The activity distribution was followed over a 24 h period.

Results: Loading efficacy of $^{212}$Pb: 34.8% (n=3).

Retention was measured by gamma spectroscopy, and more than 99% of the $^{212}$Pb was associated with the liposomes for incubation times up to 24 h.

Example 2

Retention of $^{212}$Bi Formed from the Decay of Liposome-associated $^{212}$Pb

Methods: Liposomes were loaded with $^{212}$Pb as described above. The liposome associated radioactivity was isolated by eluting the reaction mixture with 10 mM EDTA in PBS on a PD-10 column pre-equilibrated with 10 mM EDTA in PBS.

After 3 hours, in order to ensure that transient equilibrium between $^{212}$Pb and $^{212}$Bi was established, aliquots of the solution were applied to PD-10 columns pre-equilibrated with 10 mM EDTA in PBS for separation of free radionuclides from liposome-associated radionuclides. The activity distribution was followed over a 24 h period.

A separate aliquot of the labeled liposomes that did not undergo the separation procedure (of identical geometry to that obtained from chromatographical procedures) was measured for use as a standard. This was performed to establish the activity ratio of $^{212}$Bi/$^{212}$Pb at radioactive equilibrium.

Results: By comparing the ratio of $^{212}$Bi/$^{212}$Pb obtained for the chromatographically separated liposomes with that of the equilibrium mixture, it was estimated that more than 95% of the $^{212}$Bi was shown to be retained in the liposomes after the decay of liposome associated $^{212}$Pb.

Additionally, measurements of the $^{212}$Bi activity in the two chromatographically obtained fractions were compared. More than 99% of the total $^{212}$Bi activity eluted in the fractions corresponding to the liposomes.

Example 3

Investigating Possible Pb and Bi Reloading in Liposomes

Methods: Liposomes corresponding to 30–60 mM lipid, entrapping 150 mM citric acid, 30 mM DOTA, and using an external solution containing 10 mM EDTA in PBS were added to a film of the ionophore A23187 (20–26 nmol on the inside surface of a glass vial). $^{212}$Pb and $^{212}$Bi in PBS was then added followed by incubation at 37° C. Aliquots of the solution were eluted through PD-10 columns and the chromatographically obtained fractions corresponding to the liposome-eluate was assayed by the intrinsic Ge-detector.

Results: No detectable loading (<1%) of $^{212}$Pb and $^{212}$Bi was observed over a 24 h time period.

Example 4

Loading of $^{223}$Ra in Liposomes $^{223}$Ra was produced from a generator based on $^{227}$Ac as described (Larsen and Henriksen, 1999). Briefly, $^{227}$Ac and its daughter nuclide $^{227}$Th are retained in a column of an extraction chromatographic resin facilitating elution of $^{223}$Ra using a mineral acid. For incorporating radium into liposomes, the eluted solution from the generator was evaporated to dryness and $^{223}$Ra was then dissolved in 5 mM citrate, pH 7.4.

Liposomes corresponding to a lipid concentration of 30–60 mM was vigorously mixed with a film of the ionophore A23187 (10–13 nmol on the inner surface of a glass vial). Thereafter, approximately 50 kBq of $^{223}$Ra was added and the mixture incubated at 75° C. for 20 min. The reaction mixture was then added to 100 μl of 10 mM EDTA, and eluted on a PD-10 column for isolating the radioactivity associated with the lipid vesicles.

The retention of the liposome associated $^{223}$Ra was investigated by incubating the vesicles at 37° C. in human serum (Sigma) or 5 mM EDTA in human serum at a liposome concentration of 0.3 mg total lipid/ml serum. The results are exhibited in the Table 2, and demonstrate that $^{223}$Ra is very stably retained in the liposomes.

TABLE 2

| Incubation time (days) | % of total $^{223}$Ra in liposome fraction |
| --- | --- |
| 1 | 94.6 ± 1 |
| 3 | 94 ± 2.5 |
| 4 | 94.7 ± 0.5 |

Mean s.d., n = 4

Example 5

Determining if Reloading Would Contribute in the $^{223}$Ra Retention Experiment Methods: Liposomes corresponding to 30–60 mM of lipid, formed by hydration of lipid films with 150 mM citric acid, 30 mM DOTA, external solution PBS or serum were added to a film of the ionophore A23187 (10–13 nmol distributed on the inside surface of a glass vial). $^{223}$Ra in 5 mM citrate pH 7.4 was then added followed by incubation at 37° C. Aliquots of the solution were applied to PD-10 columns and the chromatographically obtained fraction corresponding to the liposomes was assayed by the intrinsic Ge-detector.

Example 6

Loading of $^{207}$Bi in Liposomes

Methods: $^{203-207}$Bi was produced by (p, xn) reactions on natural lead targets and purified by using a lead selective extraction chromatographic resin (Henriksen and Hoff, 1998).

An isotopic Bi-mixture consisting mainly of $^{205}$Bi and $^{207}$Bi, hereafter denoted as $^{207}$Bi, was used in this study. 50 μl of a solution of $^{207}$Bi in $10^{-4}$ M HCl was added to the liposomes, corresponding to 30–60 mM of lipid, which in advance had been mixed with a film of the ionophore A23187 (10–13 nmol on the inner surface of a glas vial) and incubated for 30 min at 75° C. The reaction mixture was then added 100 μl of 10 mM EDTA, and eluted on a PD-10 column to isolate the radioactivity associated with the lipid vesicles.

Results: 32% of the total $^{207}$Bi was found to be associated with the liposomes.

Example 7

Loading of $^{228}$Ac in Liposomes

Methods: $^{228}$Ac was isolated from a $^{232}$Th(NO$_3$)$_4$ preparation by a combination of solvent extraction and ion exchange. $^{232}$Th(NO$_3$)$_4$ (4H$_2$O originally) was dissolved in 20 ml 0.1 M HNO$_3$ and added to a 500 ml separation funnel and contacted with 5×100 ml of a 2 M solution of HDEHP in heptane. The aqueous phase was then washed three times with heptane and thereafter applied to a 3×40 mm column of AG50W-X12 cation exchange resin for isolation of $^{228}$Ac as described (Cabell, 1959). From the column, $^{212}$Pb, $^{212}$Bi, $^{224}$Ra and $^{229}$Ra was eluted in 3 M HNO$_3$ and the solution was left for >20 h. The solution was then evaporated to dryness followed by leaching the radionuclides from the vessel with 1 ml 1 M HNO$_3$. This solution was applied to a 3×40 mm column of AG50W-X12. Again, $^{212}$Pb, $^{212}$Bi, $^{224}$Ra and $^{228}$Ra was eluted in 3 M HNO$_3$. $^{228}$Ac was eluted in 6 M HNO$_3$ and the eluate evaporated to dryness. $^{228}$Ac was then leached form the vessel using 200 μl 5 mM HNO$_3$. Approximately 6 kBq of $^{228}$Ac was added to the liposomes containing the ionophore A23187 as described above, and incubated for 60 min at 75° C. The reaction mixture was then added to 100 μl of 10 mM EDTA, and eluted on a PD-10 column to isolate the radioactivity associated with the lipid vesicles. Fractions corresponding to more than 95% of the loaded vesicles were pooled and then eluted on a second PD-10 column. The liposomal retention of $^{228}$Ac was investigated by incubating the radiolabeled vesicles at 37° C. in human serum or PBS. The activity distribution was followed over a 24 h period.

Results: In the loading experiment 90–95% of the added $^{228}$Ac (corrected for decay during labeling and purification) was associated with the liposomes after the loading procedure. In the retention experiment more than 98% of the $^{228}$Ac was found to be associated with tho liposomes for incubation times up to 24 h.

Example 8

Loading of $^{90}$Y

Methods: $^{90}$Y was used as a tracer in this example to study the behavior of radiolabeled liposomes. $^{90}$Y and $^{90}$Sr was measured by liquid scintillation counting in this study.

$^{90}$Y was isolated from $^{90}$Sr by means of a strontium selective extraction chromatographic resin as described by Dietz and Horwitz (1992). Here, $^{90}$Sr (Amersham, Buckinghamshire, England) in 0.1 M HNO$_3$ was evaporated to dryness and residue added 3 M HNO$_3$. The solution was loaded onto a 3×20 mm column of Sr-resin (EiChroM, Darien, Ill., USA) and the column washed with 5 ml 3 M HNO$_3$.

This procedure selectively elutes $^{90}$Y while Sr is sufficiently retained on the column to lower the $^{90}$Sr content of a $^{90}Sr/^{90}Y$ mixture by a factor of approximately $10^3$ (Dietz and Horwitz, 1992), After this, $^{90}Sr$ was stripped from the column using 0.05 M $HNO_3$ and this solution was left for one week in order to allow $^{90}Y$ to grow in. Then, the solution was evaporated to dryness and the residue added 3 M $HNO_3$ before separating the radionuclides on a second column of Sr-Resin. The eluate containing $^{90}Y$ was evaporated to dryness and the radionuclide leached form the vessel using 200 µl 5 mM $HNO_3$. This solution was added to liposomes containing the ionophore A23187 (as described previously) and incubated for 60 min at 75° C., The reaction mixture was then added 50 µl 10 mM EDTA, and eluted on a PD-10 column for isolating the radioactivity associated with the lipid vesicles. The fraction corresponding to more than 95% of the vesicles was then eluted on a second PD-10 column. The liposome retention of the liposome associated $^{90}Y$ was investigated by incubating the vesicles at 37° C. in human serum or PBS. The activity distribution was followed over a 4 day-period.

Results: More than 95% of the added $^{90}Y$ was associated with the liposomes after 1 hour of loading and purification on gel exclusion column.

In the study of the liposomal retention the following results were obtained after 5 h and 1 day more than 99% was liposome associated. After 4 days the liposome associated fraction was determined to be 98±1%.

As shown in these experiments liposomes can be radiolabeled with alpha-particle and/or beta-particle emitting radionuclides and retain these nuclides well at physiological temperature.

Example 9

Preparation of Yttrium-90/Radium-223 PEGylated Liposome-folate-Fab'

F(ab'), RØ myeloma (Subclass IgG$_1$) 14 mg/ml in PBS was used for this experiment (Michalsen, Norwegian Institute of Public Health, Oslo, Norway).

Conjugation of Folic Acid to Antibodies

Folic acid.2H$_2$O was firstly dissolved in dimethyl sulfoxide (Fluka, H$_2$O content less than 0.05%). The solution was then cannulated onto activated 4 Å sieves (Fluka) and stored under an argon atmosphere in the dark for 6–10 hours. Tritium labeled folate ($^3$H-folate) was added as an aqueous solution of the potassium salt of $^3$H-folate (1% with respect to citric acid). The specific activity of the $^3$H-folate used for conjugation to protein was 7–7.5 GBq/mol.

The $^3$H-folate was activated for coupling to F(ab')$_2$ myeloma antibody by adding 10 mol equivalents of 1-ethyl-3-(3-dimethylaminopropyl) carbodiimide to the folate solution and incubating for 30 min at ambient temperature hereafter, a 30–40-fold molar excess of the activated folate was added to protein, 14 mg/ml in PBS, and allowed to react for 30–60 min. The reaction was quenched by adding 0.2 ml of 0.3 M glycine in PBS/borate, pH 8.5. The folate F(ab')$_2$ conjugate (folate-P(ab')$_2$) was separated from unreacted material using a PD-10 column preequillibrated in PBS. In order to form folate-Fab', folate-F(ab')$_2$ was incubated in 1 mM Dithiothreitol (DTT) at ambient temperature for 2 h followed by elution on a NAP-5 size exclusion column. The fraction containing folate-Fab' was deoxygenated by bubbling Argon through the solution where after the solution was immediately mixed with the liposome solution.

The extent of folic acid conjugation was determined by the $^3$H-content of the purified protein as measured by liquid scintillation counting (Beckmann LS6500) combined with spectrophotometrical readings at 280 nm.

For quantification of the liposome bound fraction of folate-Fab', a trace amount of iodinated F(ab')$_2$ was added prior to the reaction with DTT (the protein was iodinated via IodoGen according to standard procedures).

Conjugation of Labeled Antibodies to Liposomes

DSPE-PEC2000-MPB (Northern Lipids, VA, Canada), sodium salt was included at 5 mol % of total phospholipid. Liposomes were otherwise constituted and were also prepared for the ionophore mediated cation loading step in an identical manner to that described for the non-PEGylated liposomes.

After allowing the reaction mixture after the loading step to reach room temperature the liposome suspension was deoxygenated prior to adding folate-Fab' to obtain a protein concentration of 0.3–0.5 mg/ml. Lipid concentration was 1–3 mM as determined by the Bartlett phosphorous assay (Bartlett, 1958). The folate-Fab' and liposomes were allowed to react for 2 h at ambient temperature. The reaction mixture was then applied using a PD-10 column equilibrated in PBS. folate-Fab' conjugated PEG-liposomes were stored at 4° C. for 12–15 h prior to use in the folate-receptor binding assays.

Liposome-bound radioactivity was measured by a NaI well type detector correcting for the spillover in the respective channels from the doubly labeled samples. Samples of single nuclide and a mixtures of the nuclides were used as reference.

From the radioactivity measurements, the protein concentration was converted to the number of Fab' per liposome assuming a liposome size of 100 nm and $8 \cdot 10^4$ phospholipids/vesicles (Kirpotin et al, 1997) and a molecular weight of the Fab' Myeloma antibody equal to 52 000.

The cell bound radioactivity was measured by the NaI-detector (3 higher concentrations for Y-90) and liquid scintillation counting after adding Insta-Gel plus (Packard) (Table 3).

TABLE 3

Binding of $^{90}Y$-liposomes conjugated with antibodies with or without folate, to OVCAR cells.

| Added liposome/cell | % cell bound folat-negative liposomes | % cell bound folat-positive liposomes |
|---|---|---|
| $1 \cdot 10^5$ | <0.5 | 10 ± 3 |
| $1 \cdot 10^4$ | 1 ± 0.5 | 9 ± 3 |
| $1 \cdot 10^3$ | 4 ± 2 | 11 ± 2 |
| $1 \cdot 10^2$ | 5 ± 1 | 16 ± 2 |
| 10 | 8 ± 3 | 46 ± 8 |

Detection of $^3$H-folate on Liposomes

PEG liposomes (2.5 mM lipid conc.) in 20 mM HEPES/300 mM sucrose was reacted with $^3$H-folate conjugated Fab' (0.5 mg/ml in PBS, folate/Fab' ratio of 2±0.2). After 2 h at room temperature, the folate-Fab' coupled liposomes were isolated by elution on a column of Sepharose CL-4B. The amount of $^3$H-folate-Fab' on the liposomes wag quantified by liquid scintillation counting of the chromatographically obtained fractions, and the folate-Fab'/liposome ratio was determined to be approximately 110.

ABBREVIATIONS

DSPC: distearoyl phosphatidyl choline
DOTA: 1,4,7,10 tetraazacyclododecane 1,4,7,10 N, N', N", N'" tetraacetic acid
DSPE-PEG2000-MPB: N-(4-(p-Maleimidophenyl)butyryl)-1,2-distearoyl-sn-glycero-3-phosphoethanolamine (Northern Lipids, VA, Canada).

HEPES: N-2-hydroxyethylpiperazine-N'-2 ethanesulphonic acid
PBS: phosphate buffered saline
EDTA: ethylene diamine N, N' tetra acetic acid
HDEHP: bis(2-ethyl hexyl) phosphoric acid
PEG: poly etylene glycol
DTT: dithiotreitol

REFERENCES

Bartlett G R. Phosphorus assay in column Chromatography. J. Biol. Chem. 234 (3), 466–468 (1958).

Cabell M J. The purification, determination and neutron capture cross section of actiniuim-227, Can. J. Chem. 37, 1094–1101, (1959).

DeVita Jr V T, Hellman S, Rosenberg S A. Cancer. Principles & practice of oncology. 5th edition Lippincot-Raven, Philadelphia, N.Y., USA (1997).

Dietz M L and Horwitz E P. Improved chemistry for the production of Y-90 for medical applications. Appl. Radiat. Isot. 43, 1093–1101 (1992).

Forssen E A. The design and development of DaunoXome® for solid tumor targeting in vivo. Adv. Drug Delivery Rev. 24, 133–150 (1997).

Gabizon R, Horowitz A T, Goren D, Tzemach D, Mandelbaum-Shavit F, Quasen M M, and Zalipsky S. Targeting Folate receptor with folate linked to extremities of poly(ethylene glycol)-grafted liposomes: In vitro studies. Bioconjugate Chem. 10, 289–298 (1999).

Gabison A. Liposome circulation time and tumor targeting: Implication for cancer chemotherapy. Adv. Drug Delivery Rev. 16, 285–294 (1995).

Gaze M N. The current status of targeted radiotherapy in clinical practice. Phys. Med. Bol. 41, 1895–1903 (1996).

Goins B. Phillips W T, and Klipper R. Repeat injection studies of technetium-99m labeled PEG-liposomes in the same animal. J. Liposome Res. 8(2), 265–281 (1998).

Hall E. Radiobiology for the radiologist. Fourth Edn. JB Lippincott Company, Philadelphia, USA (1994).

Hassfjell S P and Hoff P. A generator for production of Pb-212 and Bi-212. Appl. Radiat. Isot. 45, 1021–1025 (1994).

Henriksen G and Hoff P. Isolation of cyclotron produced Bi-205, Bi-206 and Pb-203 using a lead-selective extraction chromatographic resin. Appl. Radiat. Isot. 49, 357–359 (1998).

Hwang K J and Mauk M R. Fate of lipid vesicles in vivo: A gamma-ray perturbed angular correlation study. Proc. Natl. Acad. Sci. USA, 74, 4991–4995 (1977).

Kirpotin D, Park J W, Hong K. Zalipsky S, Wen-Lu L, Carter P, Benz C C and Papahadjopoulos D. Sterically stabilised Anti-HER2 Immunoliposomes: Design and targeting to human breast cancer cells in Vitro, Biochemistry, 36, 66–75, (1997).

Kostarelos K, Emfietzoglou D and Stamatelou M. Liposome-mediated delivery of radionuclides to tumor models for cancer radiotherapy: A quantitative analysis. J. Liposome Res. 9 (3), 407–424 (1999).

Kranz, D M, Roy, E J and Patrick, T A. Conjugates of folate anti-effector cell antibodies, U.S. Pat. No. 5,547,668 (Aug. 20, 1996).

Larsen R H, Akabani G, Welsh P and Zalutsky M R. The cytotoxicity and microdosimetry of astatine-211-labeled chimeric monoclonal antibodies in human glioma and melanoma cells in vitro. Radiat. Res. 149, 155–162 (1998).

Larsen R H, Henriksen G. Norwegian Patent application No P990001 (1999).

Lee R J and Low P S. Delivery of liposomes into cultured KB cells via folate receptor-mediated endocytosis. J. Biol. Chem. 269. 3198–3204 (1994).

MacDonald R C, MacDonald R I, Menco BPhM., Takeshita K, Subbarao N K and Hu Lan-rong. Small-volume extrusion apparatus for preparation of large, unilamellar vesicles. Bioch. Biophys. Acta 1061, 297–303 (1991).

Maruyama K, Takizawa T, Takahashi N, Tagawa T, Nagaike K and Iwatsuru M, Targeting efficiency of PEG-immunoliposome-conjugated antibodies at PEG terminals. Adv. Drug Delivery Rev. 24, 235–242 (1997).

Mauk M R and Gamble R C. Preparation of lipid vesicles containing high level of entrapped radioactive cations. Anal. Biochem. 94, 302–307 (1979).

McClure J J and Feinendegen, L E. Alpha-emitters for medical therapy: Second Bi-annual Workshop, Toronto, Canada, June 4–5, (1998). Report from Department of Energy, Germantown, Md., USA Mirzadeh S, Kumar K, Ganzow, O A. The chemical fate of 212Bi-DOTA formed by b-decay of 212Pb(DOTA)2-. Radiochimica Acta, 60, 1–10 (1993).

Ogihara-Umeda I, Sasaki T, Kojima S, Nishigori H. Optimal radiolabeled liposomes for tumor imaging. J. Nucl. Med. 37 (2), 326–332 (1996).

Olson F, Hunt C A, Szoka F, Vail W J and Papahadjopoulos D. Preparation of liposomes of defined size distribution by extrusion through polycarbonate membranes. Bioch. Biophys. Acta 557, 9–23 (1979).

Pikul II S S, Parks N J, Schneider P D. In vitro killing of melanoma by liposome delivered intracellular irradiation. Arch. Surg. 122, 1417–1420 (1987).

Reddy, J A and Low, P S. Folate-mediated targeting of therapeutic and imaging agents to cancers. *Critical Reviews in Therapeutic Drug Carrier Systems* 15 (6): 587–627 (1998)

Ritter M A, Cleaver J E, and Tobias C A. High-LET radiations induce a large proportion of non-rejoining DNA-breaks. Nature 266, 653–655 (1977).

Shinoda, T, Takagi, A, Maeda, A, Kagatani, S, Kono, Y and Hashida, M. In vivo fate of folate-BSA in non-tumour- and tumour-bearing mice. *J Pharm Sci* 87 (12): 1521–1526, 1998.

Tilcock C P, Ahkong Q F and Parr M. An improved method for the preparation of liposomal gadolinium-DTPA-Ionophore-Mediated active entrapment of gadolinium. Invest. Radiol. 26, 242–247 (1991).

Trippett, T M and Bertino, J R. Therapeutic strategies targeting proteins that regulate folate and reduced folate transport. *J Chemotherapy* 11: 3–10 (1999).

Turner A F, Presant C A, Proffitt R T, Wiliams L E, Winsor D W and Werner J L. In-111-labeled liposomes: Dosimetry and tumor depiction. Radiology 166 (3), 761–765 (1988).

Utkhede D, Yeh V, Szucs M and Tilcock C. Uptake of Yttrium-90 into lipid vesicles. Jour. Lip. Res. 4(2). 1049–1061 (1994).

What is claimed is:

1. A conjugator system, characterized in that it comprises liposomes with ionophores and with chelator located inside of the liposomes, the liposomes further encapsulating at least one heavy nuclide, wherein said heavy nuclide is an a particle emitter, $^{212}$Pb as a generator for the α-emitter $^{212}$Bi, or a mixture of an a particle emitter and $^{212}$Pb as a generator for the α-emitter $^{212}$Bi.

2. The conjugator system according to claim 1, characterized in that the concentration of chelator inside the liposomes is suitable to retain daughter nuclides resulting from decay of said heavy nuclide.

3. The conjugator system according to claim 1 or claim 2, characterized in that a chelator is selected from the group consisting of 1,4,7,10 tetraazacyclododecane-1,4,7,10 N,N',N",N'"-tetraacetic acid (DOTA),
1,4,7,10 tetraazacyclotridecane-1,4,7,10 N,N',N",N'"-tetraacetic acid (TRITA),
1,4,7,10 tetraazacyclotetradecane-1,4,7,10 N,N',N",N'"-tetraacetic acid (TETA),
1,4,7,10 tetraazacyclododecane-1,4,7,10 N,N',N",N'"-tetra (methylene) phosphonic acid (DOTMP),
1,4,7,10 tetraazacyclotridecane-1,4,7,10 N,N',N",N'"-tetra (methylene) phosphonic acid,
1,4,7,10 tetraazacyclotetradecane-1,4,7,10 N,N',N",N'"-tetra (methylene) phosphonic acid, diethylene triamine N,N',N" pentaacetic acid and isomeric derivatives thereof cryptate[2,2,2], cryptate[3,2,2], cryptate[2,2,1] and mono and di-benzo derivatives thereof, bridged calix[4]arenes containing electron rich groups selected from the group consisting of hydroxyl, carboxyl, ester, amide, and amine, 1,10 diaza-4,7,13,16-tetraoxacyclooctadecane 1,10 N,N' bis-acetic acid, and 1,10 diaza-4,7,13,16-tetraoxacyclooctadecane 1,10 N,N' bis-malonate.

4. The conjugator system according to claim 1 or claim 2, characterized in that the liposomes contain activated groups in the membrane allowing conjugation of proteins or other receptor affinic molecules to these activated groups.

5. The conjugator system according to claim 4, wherein said activated groups are poly ethylene glycol.

6. The conjugator system according to claim 1, characterized in that the liposomes are conjugated to a receptor binding protein.

7. The conjugator system according to claim 6, characterized in that the liposomes are conjugated with an IgM or IgG class antibody, or a fragment thereof or a construct from these classes of antibodies.

8. The conjugator system according to claim 6, characterized in that the liposomes are conjugated with an IgM or IgG class antibody, or a fragment thereof or a construct from these classes of antibodies, wherein the antibody, fragment, or construct is labelled with folate and at least one radionuclide.

9. The conjugator system as claimed in claim 6, wherein said receptor binding protein is a monoclonal or a polyclonal antibody, a fragment or construct thereof, or folate.

10. The method as claimed in claim 9, wherein said receptor binding protein is a monoclonal or a polyclonal antibody, a fragment or construct thereof, or folate.

11. The conjugator system according to claim 9, characterized in that the antibody or antibody fragment or construct conjugated to the liposomes is a murine, chimeric, or human monoclonal or polyclonal antibody.

12. The conjugator system according to claim 11, characterized in that the antibody or antibody fragment or construct is labelled with folate, and comprises an antigen binding site directed towards folate binding protein.

13. The conjugator system according to claim 11, characterized in that the antibody or antibody fragment or construct is labelled with folate, and comprises an antigen binding site directed towards an antigen different from folate binding protein.

14. The conjugator system according to claim 1, characterized in that the heavy nuclide is selected from the group consisting of $^{211}$At $^{212}$Bi, $^{213}$Bi, $^{212}$Pb, $^{225}$Ac, $^{223}$Ra, $^{224}$Ra, and $^{227}$Th.

15. The conjugator system according to claim 1, characterized in that the heavy nuclide is $^{212}$Pb, and said $^{212}$Pb is the generator of $^{212}$Bi.

16. A method to prepare a radiolabeled conjugator system, characterized in that liposomes with ionophores and a chelator of a suitable concentration are stably radiolabeled with a heavy α particle emitter, by mixing a solution containing at least one heavy nuclide, wherein said heavy nuclide is an α particle emitter, $^{212}$Pb as a generator for the α-emitter $^{212}$Bi, or a mixture of an α particle emitter and $^{212}$Pb as a generator for the α-emitter $^{212}$Bi, with a solution containing said liposomes, and incubating at elevated temperature compared to physiological temperature to obtain transport of the heavy nuclide into the liposomes.

17. The method according to claim 16, characterized in that the chelator is selected from the group consisting of
1,4,7,10 tetraazacyclododecane-1,4,7,10 N,N',N",N'"-tetraacetic acid (DOTA),
1,4,7,10 tetraazacyclotridecane-1,4,7,10 N,N',N",N'"-tetraacetic acid (TRITA),
1,4,7,10 tetraazacyclotetradecane-1,4,7,10 N,N',N",N'"-tetraacetic acid (TETA),
1,4,7,10 tetraazacyclododecane-1,4,7,10 N,N',N",N'"-tetra (methylene) phosphonic acid (DOTMP), 1,4,7,10 tetraazacyclotridecane-1,4,7,10 N,N',N",N'"-tetra (methylene) phosphonic acid, 1,4,7,10 tetraazacyclotetradecane-1,4,7,10 N,N',N",N'"-tetra (methylene) phosphonic acid, diethylene triamine N,N',N" pentaacetic acid and isomeric derivatives thereof, cryptate[2,2,2], cryptate[3,2,2], cryptate[2,2,1] and mono and di-benzo derivatives thereof, bridged calix[4]arenes containing electron rich groups selected from the group consisting of hydroxyl, carboxyl, ester, amide, and amine, 1,10 diaza-4,7,13,16-tetraoxacyclooctadecane-1,10 N,N' bis-acetic acid, and 1,10 diaza-4,7,13,16-tetraoxacyclooctadecane-1,10 N,N' bis-malonate.

18. The method according to claim 16 or claim 17, characterized in that the liposomes contain activated groups in the membrane allowing conjugation of proteins or other receptor affinic molecules.

19. The method according to claim 18, characterized in that the activated groups are poly ethylene glycol.

20. The method according to claim 16, characterized in that the liposomes are conjugated to receptor binding proteins.

21. The method according to claim 20, characterized in that the liposomes are conjugated with an IgM or IgG class antibody, or a fragment thereof or a construct from these classes of antibodies.

22. The method according to claim 20, characterized in that the liposomes are conjugated with an IgM or IgG class antibody, or a fragment thereof or a construct from these classes of antibodies, wherein the antibody is labelled with folate and a radionuclide or a mixture of different radionuclides, using standard procedures for folate and radionuclide labelling of the antibody.

23. The method according to claim 20, characterized in that the antibody or antibody fragment or construct conjugated to the liposomes is a murine, chimeric, or human monoclonal or polyclonal antibody.

24. The method according to claim 23, characterized in that the antibody or antibody fragment or construct is labelled with folate, and comprises an antigen binding site directed towards folate binding protein.

25. The method according to claim 23, characterized in that the antibody or antibody fragment or construct is labelled with folate, and comprises an antigen binding site directed towards an antigen different from folate binding protein.

26. The method according to claim 16, characterized in that the heavy nuclide is selected from the group consisting of $^{211}$At, $^{212}$Bi, $^{213}$Bi, $^{212}$Pb, $^{225}$Ac, $^{223}$Ra, $^{224}$Ra, and $^{227}$Th.

27. The method according to claim 16, characterized in that the heavy nuclide is $^{212}$Pb, and said $^{212}$Pb is the generator of $^{212}$Bi.

28. A pharmaceutical solution suitable for injection or infusion into a mammal, said pharmaceutical solution comprising the conjugator system according to claim 1.

29. The pharmaceutical solution of claim 28, wherein said solution is suitable for injection or infusion into a mammal by a route selected from the group consisting of intravenous, regional, and intratumoral administration.

30. A method of targeting cells expressing a folate binding protein, an estrogen receptor, or a testosterone receptor, comprising administering the pharmaceutical solution of claim 28 into a human, thereby delivering therapeutic radiation to a malignant cell expressing said folate binding protein, said estrogen receptor or said testosterone receptor.

31. The method of claim 30 wherein said malignant cell is a brain-, lung-, cervix-, ovary- or breast-cancer cell, or is derived from a leukemia, lymphoma, or malignant melanoma.

32. A kit for the preparation of the conjugator system according to claim 1, said kit comprising a vial containing a liposome solution and a vial containing a radionuclide in a solution, wherein said liposome solution and said radionuclide in solution can be mixed to facilitate radiolabeling.

33. A kit for the preparation of the conjugator system according to claim 1, said kit comprising a vial containing a liposome solution and a second vial containing a radionuclide in a solution and a third vial containing a molecule with receptor affinity, wherein said liposome solution, said radionuclide in solution, and said molecule with receptor affinity can be mixed to facilitate radiolabeling and labeling with a receptor affinic molecule.

34. The method as claimed in claim 28, wherein said mammal is a human.

35. A method for treating a malignancy in a mammal, comprising administering the pharmaceutical solution of claim 28 in combination with a therapy selected from the group consisting of radioimmunoconjugate administration, other forms of radiopharmaceutical therapy, chemotherapy, external beam therapy, and surgery, to said mammal.

* * * * *

UNITED STATES PATENT AND TRADEMARK OFFICE
CERTIFICATE OF CORRECTION

PATENT NO. : 6,592,843 B2      Page 1 of 1
DATED : July 15, 2003
INVENTOR(S) : Roy H. Larsen and Gjermund Henriksen It is certified that error appears in the above-identified patent and that said Letters Patent is hereby corrected as shown below:

Column 14,
Lines 60 and 62, replace "an a" with -- an $\alpha$ --;

Column 15,
Line 15, insert -- , -- after "thereof";
Line 45, claim 10 should depend from claim 20;

Column 16,
Line 4, replace "a particle" with -- $\alpha$ particle --; and
Lines 5 and 7, replace "an a" with -- an $\alpha$ --.

Signed and Sealed this

Thirtieth Day of March, 2004

JON W. DUDAS
*Acting Director of the United States Patent and Trademark Office*

UNITED STATES PATENT AND TRADEMARK OFFICE
CERTIFICATE OF CORRECTION

PATENT NO.     : 6,592,843 B2
DATED          : July 15, 2003
INVENTOR(S)    : Roy H. Larsen and Gjermund Henriksen It is certified that error appears in the above-identified patent and that said Letters Patent is hereby corrected as shown below:

Column 2,
Line 7, replace "Ogihar-Umeda" with -- Ogihara-Umeda --;
Line 13, replace "radionucides" with -- radionuclides --;
Line 19, replace "stabel" with -- stable --; and
Line 25, replace "mother/daughternuclide (s)" with -- mother/daughter nuclide (s) --.

Column 3,
Line 40, replace "comnplexing" with -- complexing --.

Column 4,
Line 12, 14 and 16, replace "phosphoethano lamine" with -- phosphoethanolamine --;
Line 18, replace "constucts" with -- constructs --; and
Lines 62-63, replace "substancially" with -- substantially --.

Column 10,
Line 7, replace "glas" with -- glass --; and
Line 49, replace "tho" with -- the --.

Column 11,
Line 57, replace "preequillibrated" with -- preequilibrated --.

Column 12,
Line 6, replace "poly ethylene glycol" with -- polyethylene glycol --; and
Line 7, replace "phospolipid" with -- phospholipid --.

Signed and Sealed this

Twenty-eighth Day of September, 2004

JON W. DUDAS
*Director of the United States Patent and Trademark Office*